United States Patent
Snel et al.

(10) Patent No.: US 7,697,128 B2
(45) Date of Patent: Apr. 13, 2010

(54) METHOD OF IMAGING RADIATION FROM AN OBJECT ON A DETECTION DEVICE AND AN INSPECTION DEVICE FOR INSPECTING AN OBJECT

(75) Inventors: Robert Snel, Delft (NL); Arno Jan Bleeker, Westerhoven (NL); Hedser Van Brug, Gravenhage (NL)

(73) Assignee: ASML Netherlands B.V., Veldhoven (NL)

(*) Notice: Subject to any disclaimer, the term of this patent is extended or adjusted under 35 U.S.C. 154(b) by 365 days.

(21) Appl. No.: 11/727,165

(22) Filed: Mar. 23, 2007

(65) Prior Publication Data

US 2008/0230695 A1 Sep. 25, 2008

(51) Int. Cl.
*G01N 21/00* (2006.01)
(52) U.S. Cl. .................... 356/237.5; 356/237.2
(58) Field of Classification Search .............. 356/237.5, 356/237.2, 600; 250/307, 492.2
See application file for complete search history.

(56) References Cited

U.S. PATENT DOCUMENTS

| 5,650,614 A | * | 7/1997 | Yasutake et al. | ............ 250/234 |
| 6,104,481 A | | 8/2000 | Sekine et al. | |
| 6,621,570 B1 | | 9/2003 | Danko | |
| 6,853,446 B1 | | 2/2005 | Almogy et al. | |
| 6,879,391 B1 | | 4/2005 | Danko | |
| 2007/0008519 A1 | | 1/2007 | Naftali et al. | |

FOREIGN PATENT DOCUMENTS

| EP | 0715147 A2 | 6/1996 |
| KR | 20030051928 A | 6/2003 |

OTHER PUBLICATIONS

International Search Report and Written Opinion of the International Searching Authority issued Jul. 1, 2008 in corresponding International Application No. PCT/NL2008/050164, filed Mar. 21, 2008.

* cited by examiner

*Primary Examiner*—Kiet T Nguyen
(74) *Attorney, Agent, or Firm*—Pillsbury Winthrop Shaw Pittman LLP

(57) ABSTRACT

A method of imaging radiation from an object on a detection device. The method includes directing a beam of coherent radiation to the object, scanning the beam of radiation over an angle in or out of a plane of incidence relative to the object, and imaging scattered radiation from the object on the detection device.

19 Claims, 5 Drawing Sheets

A

B

METHOD OF IMAGING RADIATION FROM AN OBJECT ON A DETECTION DEVICE AND AN INSPECTION DEVICE FOR INSPECTING AN OBJECT

FIELD

The present invention generally relates to a method of imaging radiation from an object on a detection device, and an inspection device for inspecting an object. More particularly, the present invention relates to a method and device for inspecting contamination particles on an article, such as a patterned structure, such as an EUV reticle of an extreme ultraviolet lithographic (EUV) apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive metal compound (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

Defects, such as small particles or other geometrical aberration, for example, due to surface defects on an article, for example, an article with a patterned surface, such as EUV reticles, will randomly scatter the light. By imaging a fraction of scattered radiation from the article on a detection device, the defects will light up as bright spots. The intensity of the spots is a measure of the size of the particle. Also, a substrate surface of a substrate to be patterned by a radiation beam in an EUV apparatus should be as particle free as possible. In this regard, a need arises for inspecting an article for defects. This may be done while filtering out higher order diffractions that arise from periodic patterns that can be present on the article. This filtering can be done by introducing a spatial filter in a Fourier plane of an imaging system that images the aforesaid fraction. However, this introduces a need for coherent light, so that the diffractions can be filtered. Generally, the use of coherent light may introduce a problem of possible speckle formation, which may arise due to surface irregularities, even when in the order of less than 1 nm.

SUMMARY

It is desirable to retain coherent light while providing a filter for surface speckle formation.

According to an aspect of the invention, there is provided a method of imaging radiation from an object on a detection device. The method includes directing a beam of coherent radiation to the object, scanning the beam of radiation over an angle in or out of a plane of incidence relative to the object, and imaging scattered radiation from the object on the detection device.

According to another aspect of the invention, there is provided an inspection device constructed and arranged to inspect an object for defects or particles. The inspection device includes an optical system constructed and arranged to direct a beam of coherent radiation to the object. The optical system includes an angle scanning element constructed and arranged to vary an incidence angle of the beam of radiation relative to the object so as to scan the beam of radiation over an angle in or out of a plane of incidence relative to the object, and a detection device constructed and arranged to receive scattered radiation from the object.

According to a further aspect of the invention, there is provided a lithographic apparatus that includes a support constructed and arranged to support a patterning device. The patterning device is capable of imparting a radiation beam with a pattern in its cross-section to form a patterned radiation beam. The apparatus also includes a substrate table constructed and arranged to hold a substrate, a projection system constructed and arranged to project the patterned radiation beam onto a target portion of the substrate, and an inspection device constructed and arranged to inspect the patterning device and/or the substrate for defects or particles. The inspection device includes an optical system constructed and arranged to direct a beam of coherent radiation to the patterning device and/or the substrate. The optical system includes an angle scanning element constructed and arranged to vary an incidence angle of the beam of radiation relative to the patterning device and/or the substrate so as to scan the beam of radiation over an angle in or out of a plane of incidence relative to the patterning device and/or the substrate. The inspection device also includes a detection device constructed and arranged to receive scattered radiation from the patterning device and/or the substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
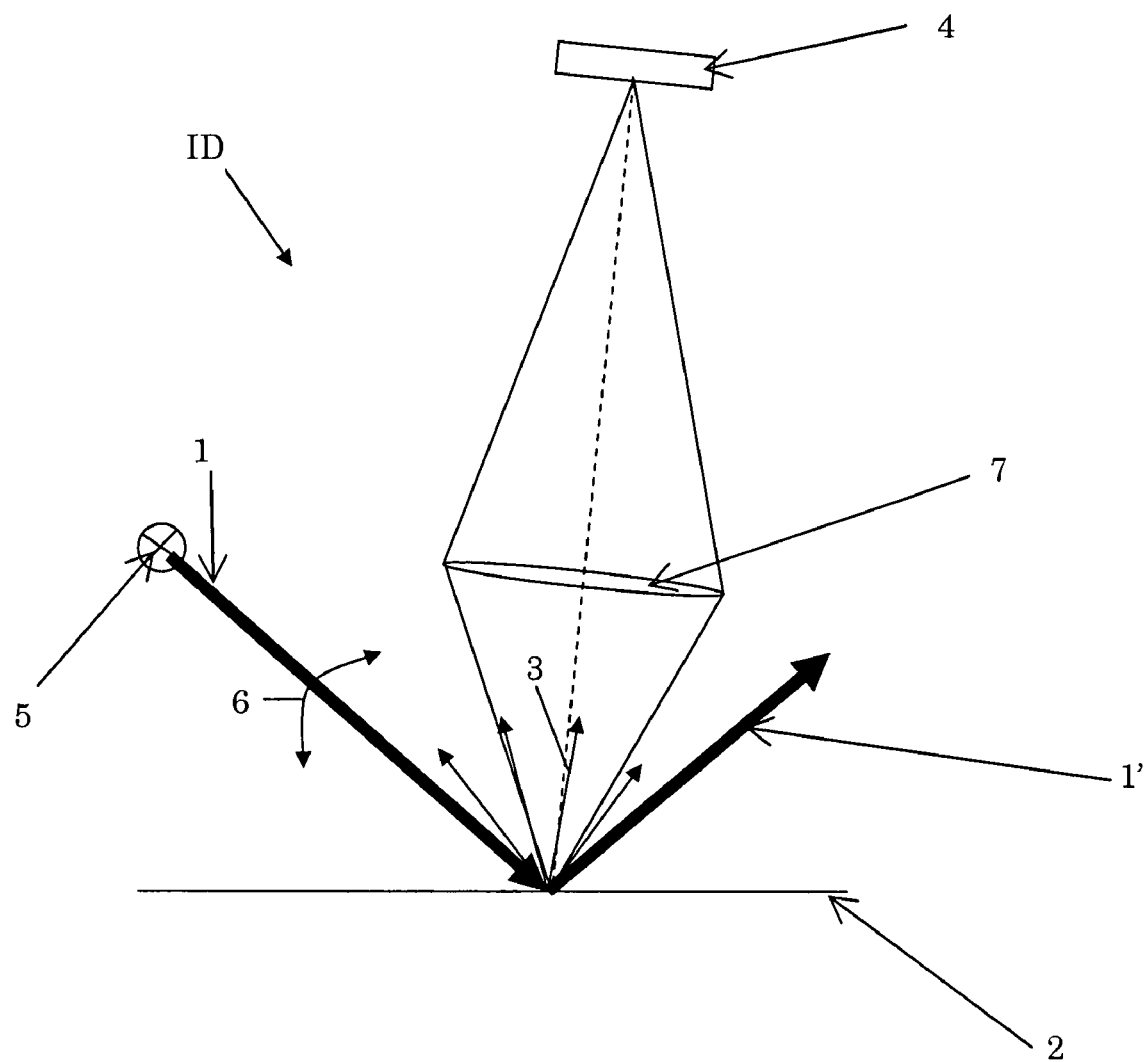
FIG. 1 shows a first schematic illustration of an embodiment of an inspection device according to the invention.

FIG. 1 shows an embodiment of an inspection device ID in which a beam of coherent radiation 1 is directed to an object 2 by an optical system 5 that is constructed and arranged to provide the beam of radiation and guide the beam of radiation 1 appropriately. The coherent radiation may be produced by a laser. The radiation 1 is reflected on object 2 and a small fraction 3 is scattered from the object 2 by variations in the object surface 2. These variations may be caused by substrate surface variations and/or particles that may be present on the surface. There is a trade off between particle size (signal) to substrate smoothness and detection speed (noise). Signal and noise histograms typically have a normally distributed patterns. Detection reliability increases when both histograms are separated. One noise contribution is created by "speckle", which is the interference of coherent light reflected by the substrate surface nano-structure. Even the smoothest surfaces, such as EUV reticles, can produce speckle. The easiest way to reduce speckle is to apply non-coherent light. However, in some instances, for example due to lack of space and/or since the coherent light may be desired for other purposes such as spatial filtering, this may not be possible. Therefore it is desirable to suppress speckle while retaining coherent light as incident light on the object surface 2. To this end, according to an aspect of the invention, it is proposed to scan the beam of radiation 1 over an angle of incidence relative to the object 2. The angle of incidence may be quite small but may vary in a range of about 40° to about 80° in or outside a plane of incidence. Generally, the beam of radiation may qualify as a grazing incident beam of radiation. By scanning the beam of radiation over an angle of incidence, the surface variations that arise due to surface irregularities, in particular the sub-nanometer smoothness variations, will vary in angle and therefore will be projected on relatively different locations by imaging element 7. Thus, the speckle will be distributed and this will cause a variation, which may be a result from the scattering of the particle that has a size that may be in a sub 100 nanometer range, for example 20 to 70 nanometers. In one embodiment, the variations are "recorded" by a applying a scanning rate of the scanning beam that will be higher than an image frame rate so that the image is smoothed from the speckle. Accordingly, the detection device 4 is arranged for receiving a fraction 3 of scattered radiation. The angle scanning element will be further discussed with reference to FIG. 4 below, but generally may comprise a vibrating mirror or the like.

Figure 2:
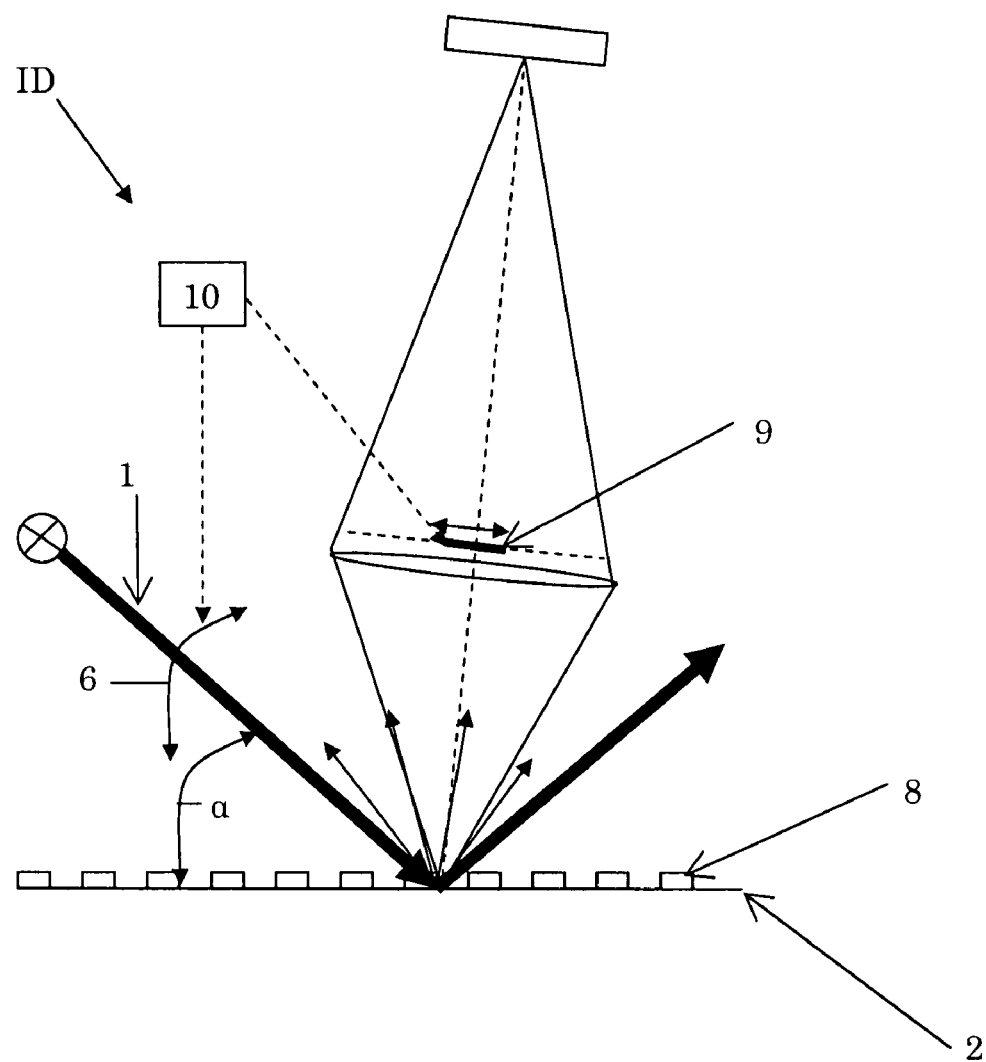
FIG. 2 shows another embodiment of the inspection device according to the invention.

FIG. 2 shows another embodiment of the inspection device ID. Although the speckle filtering method according to embodiments of the invention is not limited to periodic structures such as reticle pattern structures 8, a potential advantage of the embodiments of the invention is that for periodic structures 8, the reflections will cause diffraction of a periodic nature so that the periodic pattern will generate a fixed Fourier pattern. The particles on those patterns, such as contamination particles, can be detected by suppressing the Fourier patterns. The angle-scanning element 6 as described above will cause a translating or widened Fourier pattern; which may impair a signal noise ratio.

In this respect, a spatial filtering can be applied for filtering a diffraction order of the periodic structure 8 provided on the object 2. The signal noise ratio can be improved by synchronizing the spatial filtering by the spatial filter 9 with the scanning movement of the angle-scanning element 6 to optimize a light yield and improve a signal noise ratio. Accordingly, a vibrating Fourier filter 9 may be provided that is synchronized with the incident beam 1 having a varying angle of incidence α. To this end, a synchronizer 10 is provided to synchronize the spatial filter 9 with the angle-scanning element 6. In one embodiment the spatial filter 9 may be provided as an adaptive filter that is adaptively associated with the pattern structures 8 and that is translated in synchronization with incident radiation beam 1. The filter may be provided on a number of positions but is generally situated out of an imaging plane such as the conjugate plane relative to the object 2 and is able to specifically filter out radiation from the received radiation beam 1 that is diffracted by the patterned optical structure 8. The adaptive filter may be a micro mirror device, for example, a TI-DMD or LCD based device such as a LCOS, or reflective or LCD transmissive device. Thus, the translations may be provided mechanically or electro/optically or in any suitable way.

Figure 3:
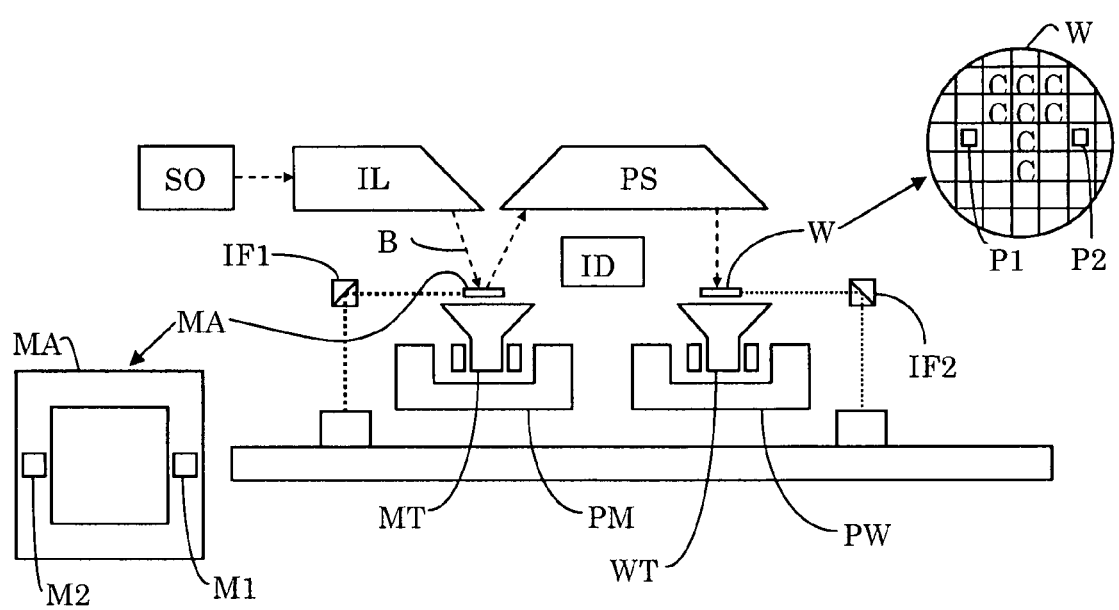
FIG. 3 depicts a lithographic apparatus according to an embodiment of the invention.

FIG. 3 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 3, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

The method and device illustrated with reference to FIGS. 1 and 2 can be applied in a number of situations, in particular to separate scattering radiation caused by different sizes of surface structures such as a sub nanometer surface variation or a contamination, which may be in the order of several nanometers or even tenths of nanometers.

Figure 4:
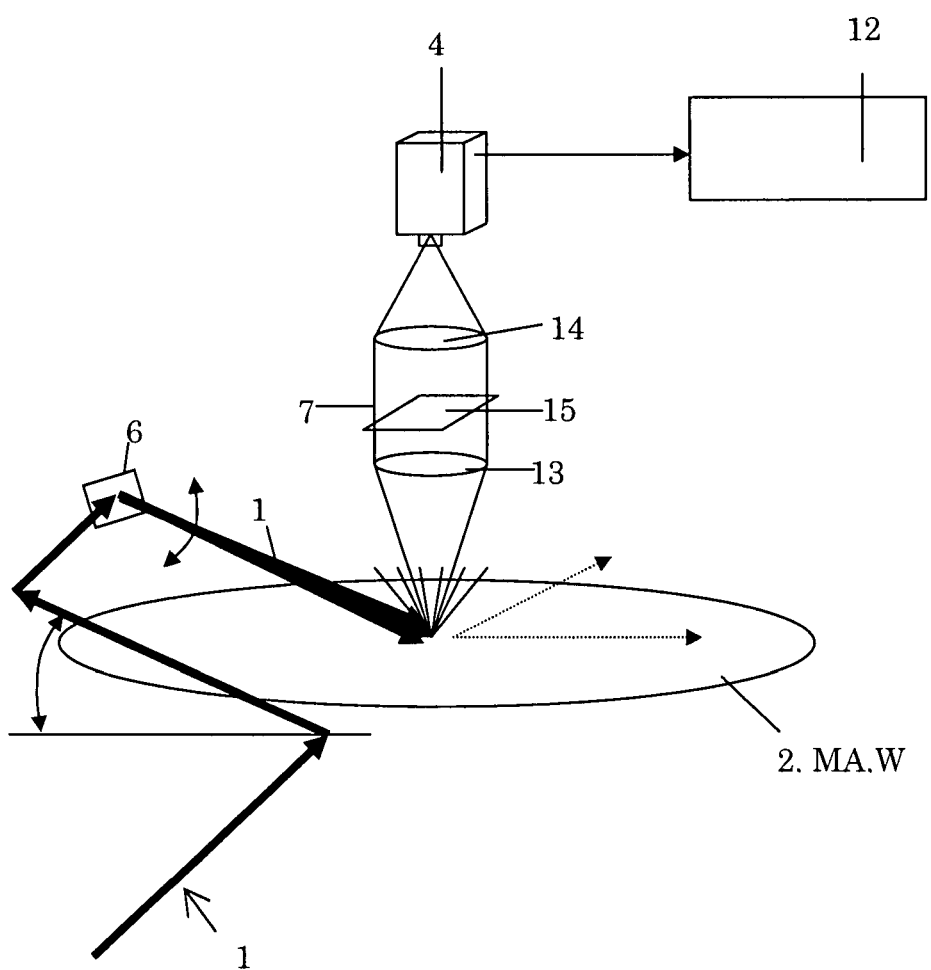
FIG. 4 illustrates another embodiment of the inspection device according to the invention.

The FIG. 4 embodiment illustrates a set-up for inspection of a wafer or reticle 2 of an EUV-apparatus such as disclosed in FIG. 3. Accordingly, this apparatus comprises a support MT constructed to support a patterning device MA, wherein the patterning device MA is capable of a imparting a radiation beam B with a pattern in cross-section to form a pattern radiation beam. In addition, a substrate table WT is constructed to hold a substrate W, which is illustrated in FIG. 4 as substrate 2, which may be a wafer or a reticle depending on application purposes. The device illustrated in FIG. 4 may be in-tool inspection device which is incorporated in the device illustrated in FIG. 3 (not shown) in particular this device is an extreme EUV-apparatus in which the patterning device is inspected, because the patterning device is susceptible to contamination, since it is not protected by a pellicle. FIG. 4 illustrates the inspection device as a separate device and it may be used for inspection purposes of object 2 which may be a mask MA as depicted in FIG. 3, prior to shipping or using in the apparatus. As an in-tool device, as shown in FIG. 3, it may perform a quick inspection of the patterning device MA and/or substrate W prior to a lithographic process. To this end a beam of radiation 1 is provided as a grazing incidence laser beam 1 directed to the object 2. The wavelength of the laser beam 1 can be any wavelength suitable for inspection purposes, in particular, not necessarily although not excluded therefrom (EUV-light). Typically, unless specified otherwise, the term "light" or "radiation" is used to indicate any electromagnetic radiation of a suitable wavelength. For the purposes of application, in the embodiments, visible or near visible light may be used for inspection purposes.

A contamination can be detected by comparing the imaged fraction of scattered light 3 where the predetermined image or predetermined data available in computer 12, so as to identify scattered radiation representative of contamination particles. In the embodiment depicted in FIG. 4 the optical system 7 is provided by lenses 13 and 14 in combination with a polarizing element 15. The angle-scanning element 6 is provided by a vibrating mirror and vibrates in a suitable way to scan the beam of radiation 1 over angle of incidence relative to the object 2. As an alternative the angle-scanning element 6 may comprise a moveable optical element having a varying refractive surface such as a "wobbly" element also it may have a varying reflective surface. The detection device 4 is preferably coded by Peltier elements to further suppress noise.

Figure 5:
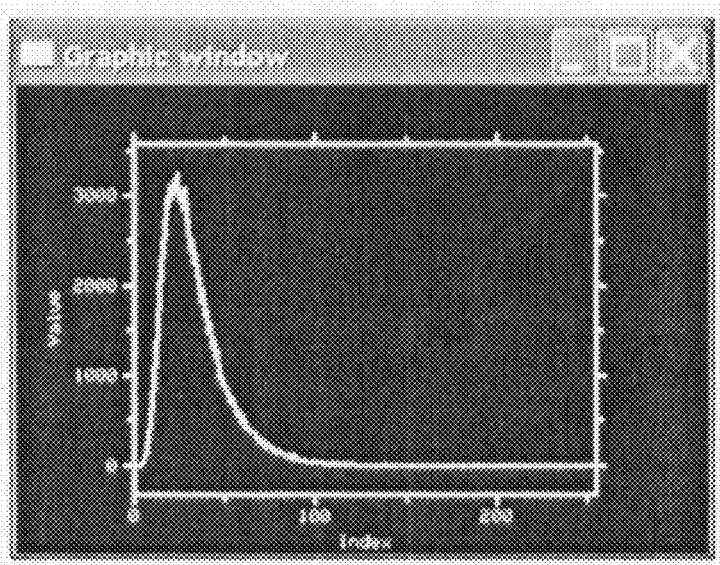
FIGS. 5A and 5B show graphs that show an improved signal noise ratio using a method according to an aspect of the invention.
Figure 5:
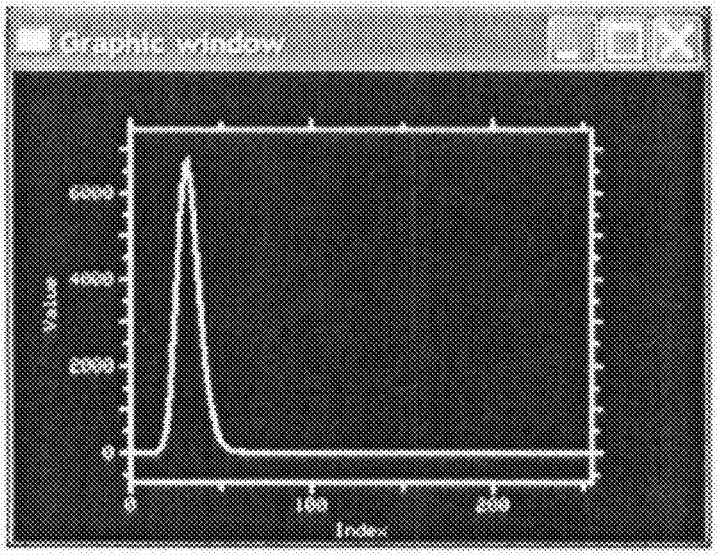

FIG. 5 shows an illustrative graph of a histogram above FIG. 5A (without the inventive speckle suppression method), and a graph below FIG. 5B (with the inventive speckle suppression method). It can be clearly seen that the Signal noise ratio is dramatically increased. By changing the angle of incidence, even in a range of μrad, the resulting changes in speckle suppression can be of considerable impact. The vibrating-angle is vibrating several circles per CCD integration period, thus averaging the surface-roughness-induced-speckle while retaining the particle-scattering. The signal noise ratio improvement may be of a factor 10, and calculations show that a factor of 100-500 may be feasible.

Therefore a faster, more reliable detection of smaller particles (in the sub 30 nm range) on substrates with- or without periodic patterns may be feasible in real life lithographic processing conditions.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

While the invention has been illustrated in the context of particle detection for extreme ultraviolet lithographic processing purposes, it will be clear to the skilled person that the method is not limited thereto but may be applied in any context wherein the need for speckle reduction is present, while retaining coherence of the beam in at least a part of an imaging system.

Furthermore the invention method can be applied with other angle scanning element positions, for example more than one mirror or an arrangement having an incident beam angle rotating around the inspection focus.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A method of imaging radiation from an object on a detection device, said method comprising:
   directing a beam of coherent radiation to said object;
   scanning said beam of radiation over an angle in or out of a plane of incidence relative to said object; and
   imaging scattered radiation from said object on said detection device.

2. A method according to claim 1, wherein said angle of incidence is varied in a range of about 40° to about 80°.

3. A method according to claim 1, wherein a scanning rate of said scanning beam is higher than an image frame rate of the detection device.

4. A method according to claim 1, further comprising spatially filtering a diffraction order of a periodic structure provided on said object.

5. A method according to claim 4, further comprising synchronizing said spatial filtering with said scanning so as to optimize a light yield of said scattered radiation.

6. A method for inspecting an object for defects, the method comprising:
    directing a beam of coherent radiation to said object;
    scanning said beam of radiation over an angle in or out of a plane of incidence relative to said object;
    imaging scattered radiation from said object on a detection device;
    comparing an image of said scattered radiation with a predetermined image; and
    identifying scattered radiation representative of defects or particles.

7. An inspection device constructed and arranged to inspect an object for defects or particles, the inspection device comprising:
    an optical system constructed and arranged to direct a beam of coherent radiation to said object, said optical system comprising an angle scanning element constructed and arranged to vary an incidence angle of said beam of radiation relative to said object so as to scan said beam of radiation over an angle in or out of a plane of incidence relative to said object; and
    a detection device constructed and arranged to receive scattered radiation from said object.

8. A device according to claim 7, wherein said angle scanning element comprises a tiltable mirror.

9. A device according to claim 7, wherein said angle scanning element comprises a movable optical element having a varying refractive surface.

10. A device according to claim 7, further comprising a spatial filter constructed and arranged to filter a diffraction order of a periodic structure provided on said object.

11. A device according to claim 10, further comprising a spatial filter movement synchronizer constructed and arranged to synchronize said spatial filter with said angle scanning element.

12. A device according to claim 10, wherein said spatial filter comprises an adaptive filter associated with said patterned structure.

13. A device according to claim 10, wherein said spatial filter is in a conjugate plane relative to said object so as to filter out radiation from said received radiation beam that is scattered by said patterned optical structure.

14. A device according to claim 10, wherein said spatial filter is an adaptive filter adapted according to a predetermined filter pattern according to said patterned structure.

15. A device according to claim 14, wherein said spatial filter is a micro mirror device.

16. A device according to claim 15, wherein said micro mirror device is a TI-DMD or an LCD based device, a reflective device, or an LCD transmissive device.

17. A device according to claim 7, wherein said radiation beam is provided as a grazing incidence laser beam of visible or near visible light.

18. A lithographic apparatus comprising:
    a support constructed and arranged to support a patterning device, the patterning device being capable of imparting a radiation beam with a pattern in its cross-section to form a patterned radiation beam;
    a substrate table constructed and arranged to hold a substrate;
    a projection system configured to project the patterned radiation beam onto a target portion of the substrate; and
    an inspection device constructed and arranged to inspect said patterning device and/or said substrate for defects or particles, said inspection device comprising
        an optical system constructed and arranged to direct a beam of coherent radiation to said patterning device and/or said substrate, said optical system comprising an angle scanning element constructed and arranged to vary an incidence angle of said beam of radiation relative to said patterning device and/or said substrate so as to scan said beam of radiation over an angle in or out of a plane of incidence relative to said patterning device and/or said substrate, and
        a detection device constructed and arranged to receive scattered radiation from said patterning device and/or said substrate.

19. A lithographic apparatus according to claim 18, wherein said lithographic apparatus is an extreme ultraviolet apparatus, and wherein said patterning device comprises a reflective mask contained in a vacuum container.

* * * * *